(12) United States Patent  
Ludlow

(10) Patent No.: US 8,310,555 B2  
(45) Date of Patent: Nov. 13, 2012

(54) GOGGLE WITH A BUILT-IN CAMERA

(76) Inventor: Marcus Ludlow, Wasaga Beach (CA)

( * ) Notice: Subject to any disclaimer, the term of this patent is extended or adjusted under 35 U.S.C. 154(b) by 998 days.

(21) Appl. No.: 12/137,562

(22) Filed: Jun. 12, 2008

(65) Prior Publication Data

US 2009/0307828 A1 Dec. 17, 2009

(51) Int. Cl.
*H04N 5/232* (2006.01)
(52) U.S. Cl. .............. 348/211.14; 348/143; 348/151
(58) Field of Classification Search ............ 348/81, 348/82, 143, 151, 211.14, 231.7, 373, 376, 348/451, 374, 375; 345/7, 8, 9
See application file for complete search history.

(56) References Cited

U.S. PATENT DOCUMENTS

| 4,414,693 | A  | * | 11/1983 | Brody ........................ 2/435 |
| 5,018,223 | A  | * | 5/1991  | Dawson et al. ............... 2/436 |
| 5,886,739 | A  | * | 3/1999  | Winningstad ............... 348/158 |
| 6,549,231 | B1 | * | 4/2003  | Matsui ........................ 348/61 |
| 6,717,737 | B1 | * | 4/2004  | Haglund ..................... 359/631 |
| 6,977,671 | B1 | * | 12/2005 | Kitson et al. ................. 348/81 |
| 7,576,800 | B2 | * | 8/2009  | Swain ......................... 348/376 |
| 2006/0109350 | A1 | * | 5/2006  | Yeh ......................... 348/207.99 |
| 2007/0030442 | A1 | * | 2/2007  | Howell et al. ............... 351/158 |
| 2007/0248238 | A1 | * | 10/2007 | Abreu ......................... 381/381 |
| 2008/0192114 | A1 | * | 8/2008  | Pearson et al. ............... 348/81 |

* cited by examiner

*Primary Examiner* — Aung S Moe
*Assistant Examiner* — Chriss Yoder, III
(74) *Attorney, Agent, or Firm* — Nasser Ashgriz

(57) ABSTRACT

The present invention relates to goggles, in particular to ski and scuba diving goggles, with a digital camera. The camera, including the image receiving lens, digital storage, control devices and the battery units, is an integral part of the goggle. The camera and its accessories are imbedded into the goggle such that there is minimal deviation of the shape of the goggle from conventional goggles.

3 Claims, 7 Drawing Sheets

GOGGLE WITH A BUILT-IN CAMERA

FIELD OF THE INVENTION

The present invention relates to a goggle with a built-in camera and its accessories, comprising a lens, an imager, a data storage device, a battery, and camera control switches as an integral part of the goggle. One embodiment of the present invention is a ski goggle having ski goggle means, and another embodiment is an underwater diving mask having means for underwater diving.

BACKGROUND OF THE INVENTION

Goggles are used in many activities to protect wearer's eyes and part of their face against harsh temperatures, wind, rain and snow, sun and bright light, and flying objects and debris. Goggles are commonly used in sports like skiing, snowboarding, tobogganing, motorcycling, and underwater diving. Goggles also have many industrial applications, such as in sand blasting and welding.

In many of the aforementioned activities, in particular, sports activities, it is desirable to be able to take pictures of the scenery or capture some of moments during the activity. For instance, during skiing, a skier may want to take a picture of a friend going down the slopes. Usually, skiers do not like to carry a camera with them, since it is bulky and may get damaged during a fall. In addition, skiers wear gloves, which make the process of picture taking very cumbersome. Therefore, skiers and like, need to have a simple method of taking pictures during their activity. The present invention relates to this need.

With the advent of miniature digital cameras, it is now possible to incorporate a camera in a goggle. For instance, a miniature camera can be imbedded inside a ski goggle with its shutter and power systems being located on the goggle itself. Therefore, skiers do not have to carry an extra camera with them, and can take a picture at any time without taking their gloves out. This makes it convenient for a skier to take pictures of the scenery during his or her travel down the slops.

Several prior arts disclose head mounted systems with camera and video capabilities. Many are designed for military application. For instance, U.S. Pat. No. 5,200,827 discloses a video display mounted to the helmet of a soldier so that the soldier can aim a weapon to a target by moving his head. U.S. Patent Application 2007/0121068 disclosed another military goggle with video capability. Also, U.S. Pat. No. 5,949,582 issued to Coombs disclosed a thermal imaging camera in combination with a goggle. Military goggles, although have variety of image capturing features, are not suitable for common usage, such as in sports.

There are also several patents on eye glasses having a camera. U.S. Pat. No. 4,516,157 issued to Campbell discloses a pair of eye glasses with a miniature video camera mounted on the frame of the glasses. U.S. Pat. No. 6,657,673 issued to Ishikawa discloses a camera mounted on a temple of a eye glasses for recording images. The signal from the camera is recorded on a device worn on the belt of the user. U.S. Patent Application 2007/0030442 by Howell et al. discloses a pair of eye glasses with a camera and other devices. Howell's glasses also comprise of a camera located on its temple and data storage device located remotely, either on the person's body or at a distant location.

Prior arts also disclose underwater imaging systems, such as U.S. Pat. No. 6,181,644 issued to Gallagher, which discloses a scuba facemask with an imager which has a display on the lens of the facemask and the power and other accessories are connected to the body of the diver. U.S. Patent Application 2005/0237386 by Sandos discloses a scuba goggle with a detachable camera. The camera is not embedded into the mask and the whole system is bulky.

The prior art disclosing eye glasses with cameras are not designed for sports in demanding environments, such as skiing. For instance, they do not provide the proper protection for a skier. Another disadvantage of the prior art is that the camera and it accessories stand out of the glasses. Also, prior art glasses do not have the data storage system and battery pack right on the glasses. The camera on the eye glasses is wired to a storage system connected elsewhere on the body of the user. In addition, the prior art disclosing diver masks for underwater imaging are not as versatile and easy to use as the present invention.

The prior art taken either singly or in combination, is seen not to describe the instant invention as claimed.

SUMMARY OF THE INVENTION

The present invention pertains to a goggle with a digital camera and its accessories comprising a storage device, battery and electronics. In particular, one embodiment of the present goggle can be used in skiing and another embodiment of the goggle can be used in underwater diving.

One object of the present invention is to provide an imaging system for activities that utilize goggles and masks, such as skiing and underwater diving.

Another object of the present invention is to provide a goggle with an easy to use camera. For instance, skiers should not take out their ski gloves to take a picture. They should be able to take a picture by just clicking a button on their goggle.

Another object of the present invention is to provide a goggle that is not obviously altered from conventional goggles. Skiers do not wish to wear goggles which make them look like a "robot". A ski goggle with a camera should not have features that stand out and should be streamlined with the goggles main function, which is to protect the eyes and the face of the wearer.

Wearer's of goggles, such as ski goggles, require comfort above all. Therefore, another object of the present invention is to provide a goggle with a camera, which is comfortable to wear. The prior art goggles and glasses that have camera attachments are not comfortable to wear, especially with activities in demanding environments, such as skiing.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION OF THE INVENTION

Before explaining the present embodiments in detail, it is to be understood that the embodiments are not limited to the particular embodiments and that it can be practiced or carried out in various ways.

Figure 1:
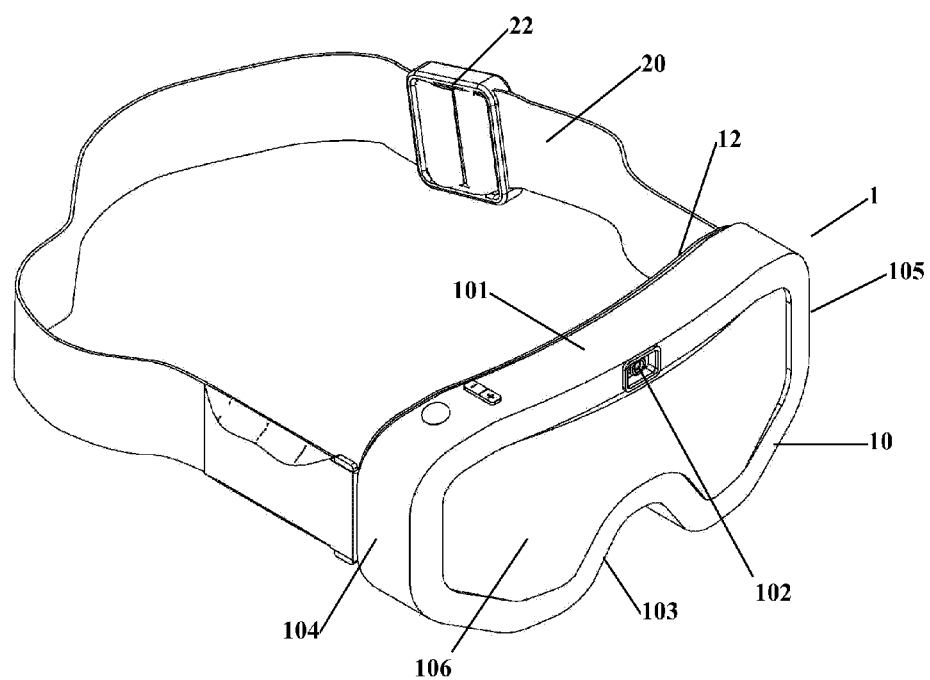
FIG. 1 illustrates one embodiment of the invention with a camera.

The present invention can be used with any type of conventional goggle, in particular with a ski goggle. One embodiment of the present invention, illustrated in FIG. 1, is a ski goggle with a built-in camera. A ski goggle 1 comprises of a frame 10, made of a resilient flexible material, normally a soft plastic or a soft rubber like material. The frame is usually made by injection molding process and comes in one piece. Conventional goggles are curved to conform to the face of the user in the area of the user's eyes. In order to make the goggle comfortable for the user, the part of the goggle that lies on the face of the user is provided with a flexible padding or soft cushioning material 12, typically made of foamed plastic, foamed rubber or very soft plastic material which is cemented or otherwise secured to the frame. Ski goggles also have vent apertures (not shown here) to allow for air circulation and prevent fogging of the goggle due to moisture. Vent apertures are usually covered by a porous foam to allow for air flow, yet preventing flow of other particles, rain and snow. Another feature of a ski goggle is its special lens. A double lens system with vacuum in between is typically used to prevent fogging.

FIG. 1 illustrates a flexible frame 10, which includes a top portion 101, a top-front portion 102, a bottom portion 103, and first 104 and second 105 side portions. A lens (not shown here) is usually removable mounted at the front opening 16 of the frame to protect wearer's eyes.

An elastic head band strap 20 attaches to both sides of the frame 10 to secure the goggle to the wearer's head or back of a helmet. Elastic straps are typically made of synthetic cloth interwoven with rubber material. Typically the strap includes a buckle adjustment 22 in order to vary the length of the strap 20 to secure the goggle relatively snugly against the face of the wearer.

A small digital camera is installed in the goggle. A digital camera comprises of a lens for focusing on the image, a digital imager such as a CCD for digitally capturing the image, a converter for producing digital image signals from the image captured on the imager, a digital storage device to store captures images, a battery, electrical connectors to transfer the digital image signals to the storage device, a digital display screen, and camera control switches to turn camera on and off, zooming the lens, and taking a picture, and data storage devices. Digital cameras are known to the art and are not described further.

Figure 2:
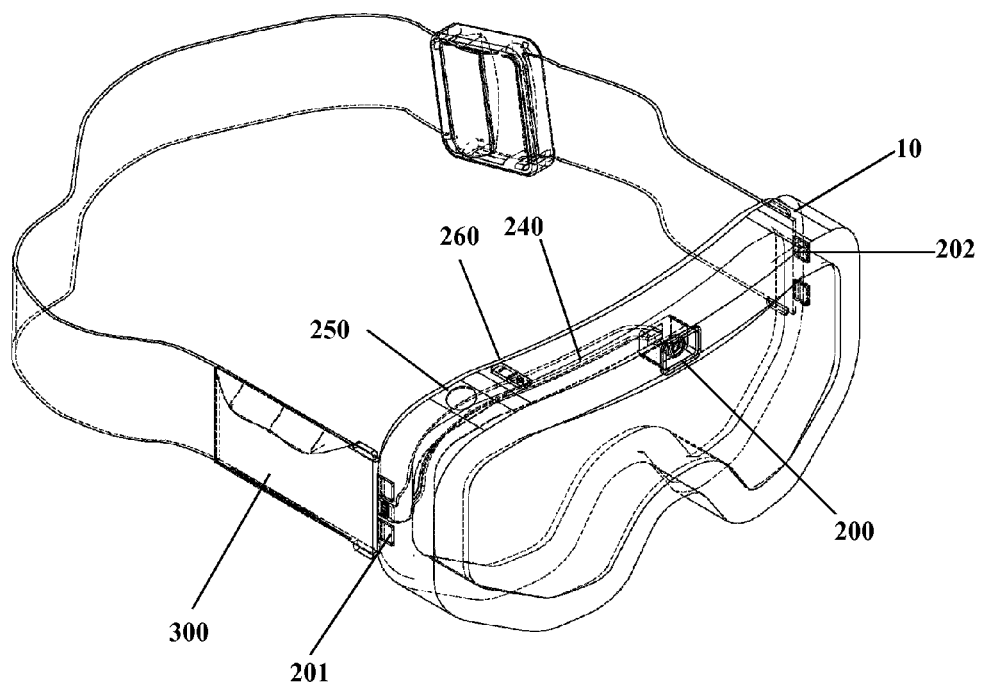
FIG. 2 illustrates the internal electronics of one embodiment of a goggle with a camera.
Figure 3:
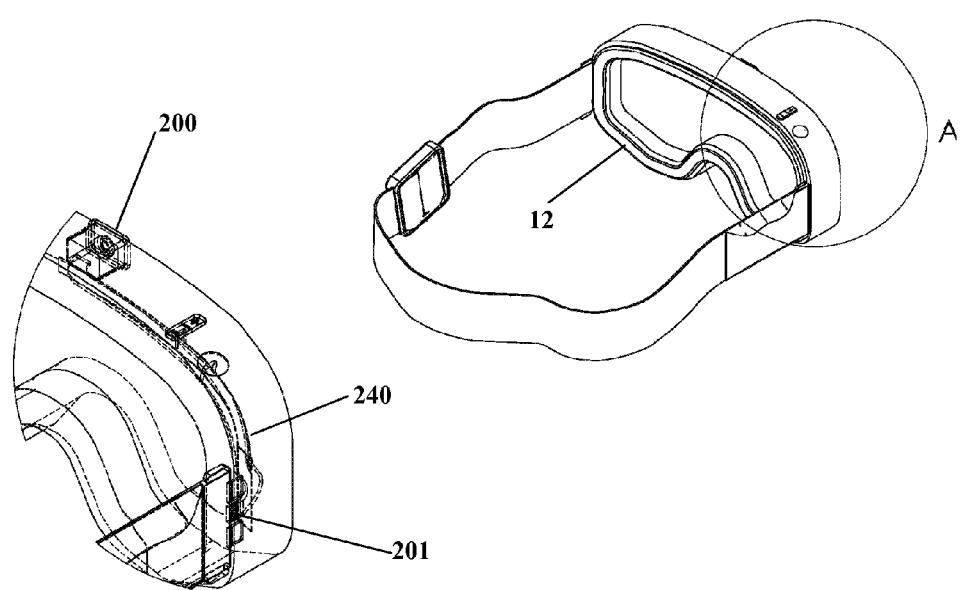
FIG. 3 illustrates a back view of the goggle and the strap with a pocket in which to install the control unit and battery for the digital camera.
Figure 4:
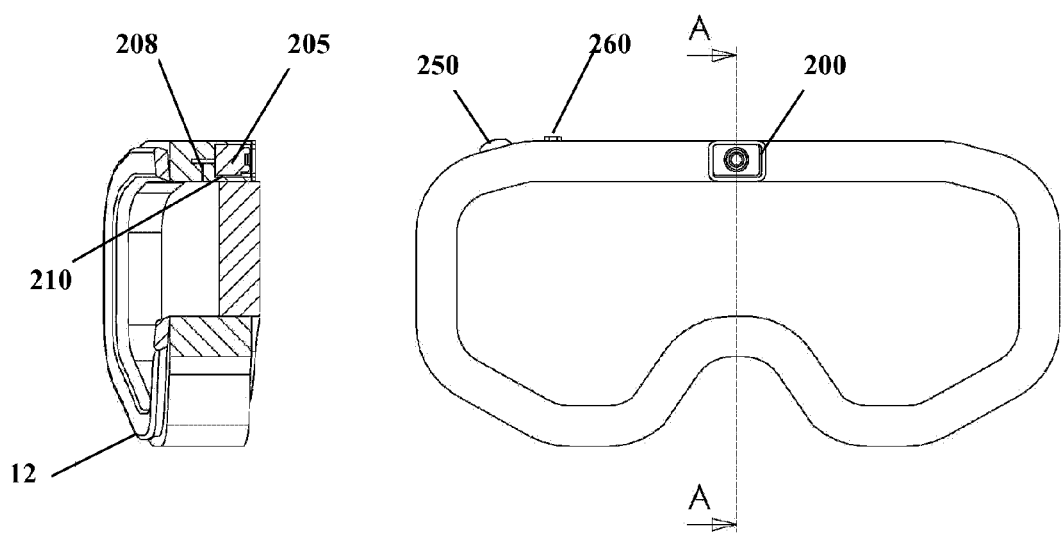
FIG. 4 illustrates the front view of the goggle and its cross sectional view showing the location of the camera.

First 104 and second 105 sides of the goggle frame 10 have first 201 and second 202 strap receiving means, respectively, as illustrated in FIGS. 2 and 3. The first side connector 201 has electrical connectors to connect to a camera control box attached to the strap 300. A miniature digital camera 200 is secured inside the frame 102 using a special housing 205 built to receive the camera, as illustrated in FIG. 4. The lens, the lens cover, the digital imager and the converter are imbedded in top-front 102 of the frame. The housing 205 is part of the frame and it may be built as one piece in the initial injection molding process. The top portion of the frame is also designed to receive electrical wirings from the digital camera to the sides of the frame to electrically connect the camera to the control box and the battery back (typically a lithium battery) located on the strap. The present embodiment includes an opening 208 on the top portion of the frame that can receive the electrical wiring 240. The frame can be flexed open from the middle opening 210 and electronics can be positioned inside the frame. This design allows for replacement of the camera and electronics if desired. All the wirings are electronic connections are water proofed.

The camera is equipped with a power on/off and an electronic shutter switch 250 as well as an electronic zoom control 260. Such control buttons and switches can be located at any location on the frame which is convenient for the wearer.

Figure 5:
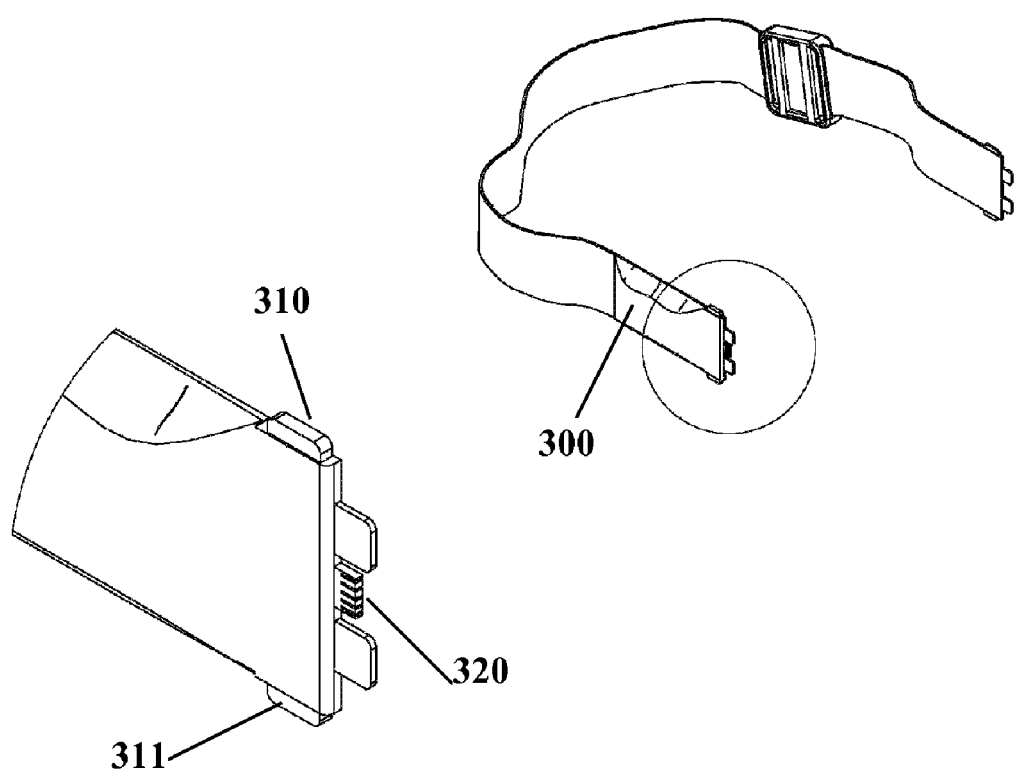
FIG. 5 illustrates one embodiment for a connection mechanism of the strap to the frame allowing for the electrical connections.

The digital camera is connected to a control and power unit placed on the strap 300. The control and power unit can be located anywhere on the strap which is convenient for the wearer. The strap is both mechanically, using any mechanical means (one shown in FIG. 5 at 310 and 311) and electronically 320 connected to the frame. In the present embodiment, the strap has a built-in pocket to receive the control/power unit. Once the control/power unit is clicked into position, it is electrically connected to the imager on the goggle frame. Other methods of connecting the control/power unit to the imager on the frame can also be use. The control and power unit can be directly connected to the wiring, without a special receiving place on the strap. The strap will then have a pocket for the control unit to slide in.

Figure 6:
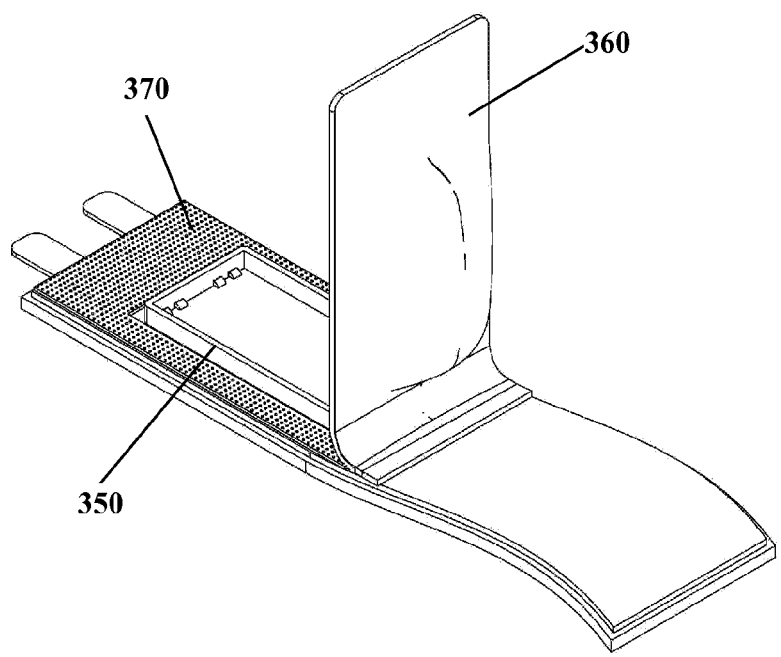
FIG. 6 illustrates the strap with a pocket to receive the digital camera control unit, storage system, and battery pack.
Figure 7:
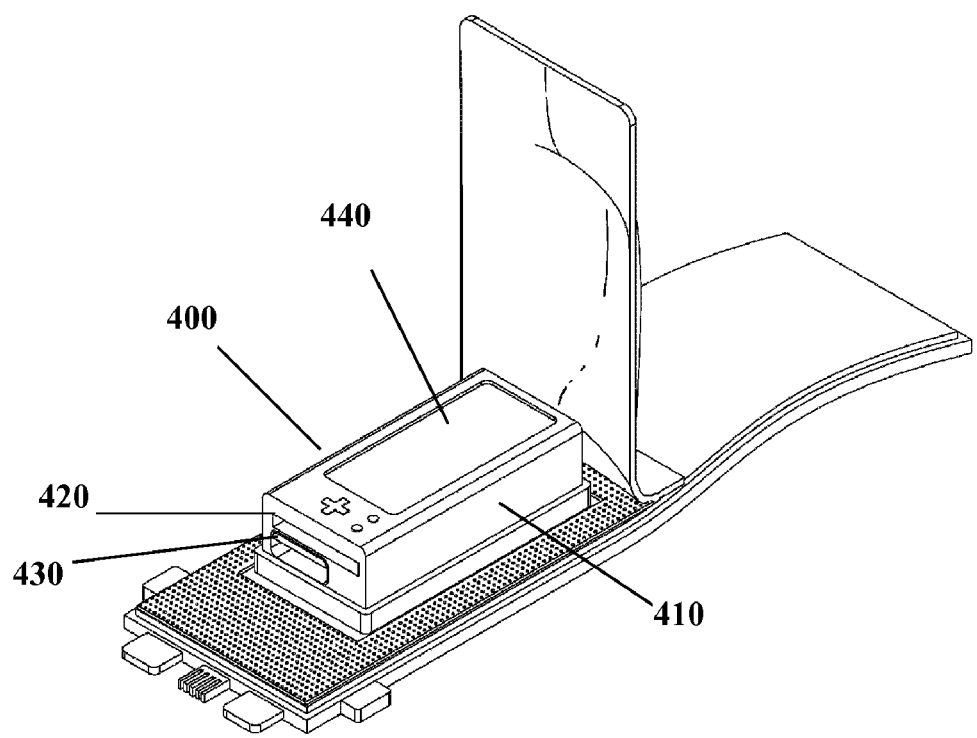
FIG. 7 illustrates the digital camera control unit comprising the electronics for the digital camera, battery pack, storage device port and the USB port.

Strap has a control unit receiving pocket 350 illustrated in FIG. 6, which can be covered by a cover 360. The control unit receiving pocket 350 preferably has a thermal insulator to prevent transfer of heat from the battery unit to the wearer's head. The cover can be tightly closed using Velcro 370 or any other means. The whole control unit receiving pocket and cover are preferably water proof. For under water masks, the pocket is made of rubber/or other water proof material and has a water proof zipper or it can be any other tightly closeable pockets.

The control box 400 comprises of a rechargeable battery 410, preferably a lithium battery, a data storage device 420, such as a SD card of a digital camera or a phone camera, a USB port 430 to download the images as well as recharging the battery unit, a display screen, such as a liquid crystal display (LCD), 440, and other standard control button known to the art. Both internal memory and external memory devices are commonly used in digital cameras, and the same can be incorporated within the present goggle.

The display screen can be located on other parts of the goggle, such as on the back of the top of the frame, or just behind the CCD camera on the top of the frame, so that the wearer can watch the image that is captures. The lens can then be adjusted to change the field of view of the camera. The camera's field of view is set to image wearer's front eye view. The camera may be mounted on an angle adjustment adjustable surface, so that its field of view can be adjusted by the wearer.

Additionally, the control box may include a mini-transmitter/receiver removable connected to the box. This system can be used to remotely transmit images to remote location.

Most digital cameras come with video and audio options, night vision options, programmable image taking or time laps photography option, automatic exposure option, autofocus option and other options known in the art. Such options can therefore be added to the goggle as well.

In another embodiment of the same invention, a goggle or a mask with built-in camera having means for underwater diving is provided. The goggle and all its electronics are waterproofed and pressure tested for underwater diving. In underwater diving masks the front lens is sealed in the frame of the mask, and the frame is seal against the face of the diver, so that the closure formed by the mask and the face of the diver is watertight. The lens of underwater masks are typically made of clear high-density plastic, glass or other like materials that provide resistance to underwater pressures. Means of providing underwater mask are known to the art and are not discussed here. All electronics in the underwater mask is waterproofed prior to installment into the mask. The switches and buttons are also watertight.

What is claimed is:

1. A ski goggle frame and strap for receiving a miniature camera and its accessories, comprising:
   a. a goggle frame having
      i. a curved frontal face to conform to the face of the skier in the area of the wearer's eyes,
      ii. a first side and a second side,
      iii. a back face to lie on the face of the wearer,
      v. a frame depth, and
      v. an upper section having a top face, a bottom face, and a central section;
   b. said frame being made of a resilient flexible material, and preferably made in one piece by injection molding;
   c. said goggle frame frontal face having an opening and adapted to receive a goggle lens;
   d. said back face further having flexible padding or soft cushioning material, preferably made of foamed plastic, foamed rubber or very soft plastic material and being cemented or otherwise secured to the frame, in order to make the goggle comfortable for the user;
   e. said central part on the upper section of the frame having an open compartment extending through the depth of the frame to receive a miniature camera;
   f. said upper section of the frame further having a closed channel longitudinally extending from the camera compartment to the first side of the goggle frame, said channel having means for opening and closing to receive electronics and electric wires, wherein said means for opening and closing said channel being a cut on one of the walls of the channel, preferably the bottom wall, allowing the channel to flex open to insert electronics and wiring, whereby electronics being kept dry;
   g. said goggle further having vent apertures to allow for air circulation and prevent fogging of the goggle due to moisture, said vent apertures being covered by a porous foam to allow for air flow, yet preventing flow of other particles, rain and snow;
   h. said first and second sides of the goggle frame having strap receiving means;
   i. said strap receiving means of said first side having electrical connectors to electrically connect to the strap;
   j. a strap having a first end and a second end, said strap ends having means to connect to the frame, wherein said means to connect to the frame comprising a side push buckle to connect the strap to the frame;
   k. said strap having means to receive camera accessories; and
   l. said strap having electrode means to electrically connect the accessories to the goggle frame, wherein said electrode means being electrodes at the central section of the buckle to electrically engage to the goggle frame,
   whereby said goggle can be used with and without a camera and its accessories.

2. The ski goggle strap of claim 1, further comprising:
   a. an elastic strap preferably made of synthetic cloth interwoven with rubber material;
   b. said strap having a buckle adjustment to vary the length of the strap;
   c. a side compartment having a base shaped to receive a digital camera control box and its accessories;
   d. said base having electrodes to electrically connect the base to said camera control box; and
   e. said side compartment of said strap having a cover to tightly close on the top of a camera control box.

3. The ski goggle frame and strap of claim 1, further comprising:
   a. a miniature digital camera having a lens for focusing on the image, a lens cover to protect the lens, a digital imager for digitally capturing the image, a converter for producing digital image signals from the image captured on the imager;
   b. a camera control box having a digital storage device to store captures images, a battery, electrical connectors to detachably transfer the digital image signals to the storage device, a digital display screen;
   c. camera control switches to turn camera on and off, zoom the lens, and take pictures and video;
   d. said lens, lens cover, digital imager and converter being imbedded in the central section of the upper part of the frame;
   e. said camera control switches imbedded in the channel in the upper part of the frame closer to the first side of the frame and extending to the top face of the frame for ease of access;
   f. said camera control box comprising of the storage devices, display screen and battery being removably attached onto said strap; and
   g. said electrical connectors of said strap receiving means being disposed within the channel in the upper section of the frame and the strap to transfer images from the camera to the storage devices on the strap.

* * * * *